United States Patent
Bruce et al.

(10) Patent No.: US 10,137,148 B2
(45) Date of Patent: *Nov. 27, 2018

(54) REDUCING THE PROLIFERATION OF ADENOCARCINOMA CELLS (CACO-2) BY ADMINISTRATION OF A POLY-OXYGENATED METAL HYDROXIDE

(71) Applicants: Erica D. Bruce, Hewitt, TX (US); John W. Woodmansee, Jr., Frisco, TX (US)

(72) Inventors: Erica D. Bruce, Hewitt, TX (US); John W. Woodmansee, Jr., Frisco, TX (US)

(73) Assignee: BAYLOR UNIVERSITY, Waco, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/984,035

(22) Filed: May 18, 2018

(65) Prior Publication Data
US 2018/0264035 A1    Sep. 20, 2018

Related U.S. Application Data

(63) Continuation-in-part of application No. 15/797,972, filed on Oct. 30, 2017, which is a continuation of
(Continued)

(51) Int. Cl.
*A61K 33/08* (2006.01)
*A61K 9/08* (2006.01)
(Continued)

(52) U.S. Cl.
CPC ............ *A61K 33/08* (2013.01); *A61K 9/0026* (2013.01); *A61K 9/08* (2013.01); *A61K 33/06* (2013.01);
(Continued)

(58) Field of Classification Search
None
See application file for complete search history.

(56) References Cited

U.S. PATENT DOCUMENTS 4,093,707 A * 6/1978 Merkl ................... A61K 8/26
423/154

OTHER PUBLICATIONS

Culver Class of 1952 Newsletter ([retrieved from on-line website: https://alumni.culver.org/document.doc?id=517&chid=63, pp. 1-20, printed Oct. 2013]). (Year: 2013).*

* cited by examiner

*Primary Examiner* — Ernst V Arnold
*Assistant Examiner* — Kyung S Chang
(74) *Attorney, Agent, or Firm* — Culhane Meadows PLLC; Robert Klinger

(57) ABSTRACT

A method of treating a mammal, comprising administering a therapeutically effective amount of a poly-oxygenated metal hydroxide composition to a mammal to reduce a proliferation of hypoxic carcinoma cells, wherein the poly-oxygenated metal hydroxide composition comprises a clathrate containing free oxygen gas ($O_2$) molecules. The carcinoma cells may comprise colon adenocarcinoma cells (CaCo-2). The poly-oxygenated metal hydroxide material is configured to provide bioavailable oxygen gas molecules to a mammal when administered to the mammal. The poly-oxygenated metal hydroxide composition can be administered intravenously, directly to carcinoma cells, and orally. The composition may comprise a fluid, where the poly-oxygenated metal hydroxide composition is soluble in the fluid.

15 Claims, 15 Drawing Sheets

Related U.S. Application Data application No. 15/346,549, filed on Nov. 8, 2016, now Pat. No. 9,801,906, which is a continuation-in-part of application No. 15/183,403, filed on Jun. 15, 2016, now Pat. No. 9,649,335.

(60) Provisional application No. 62/315,524, filed on Mar. 30, 2016.

(51) Int. Cl.
| | | |
|---|---|---|
| *A61K 47/02* | (2006.01) | |
| *A61K 9/00* | (2006.01) | |
| *A61K 33/06* | (2006.01) | |
| *A61K 47/69* | (2017.01) | |
| *A61K 47/52* | (2017.01) | |

(52) U.S. Cl.
CPC ............. *A61K 47/02* (2013.01); *A61K 47/52* (2017.08); *A61K 47/6921* (2017.08); *A61K 47/6923* (2017.08)

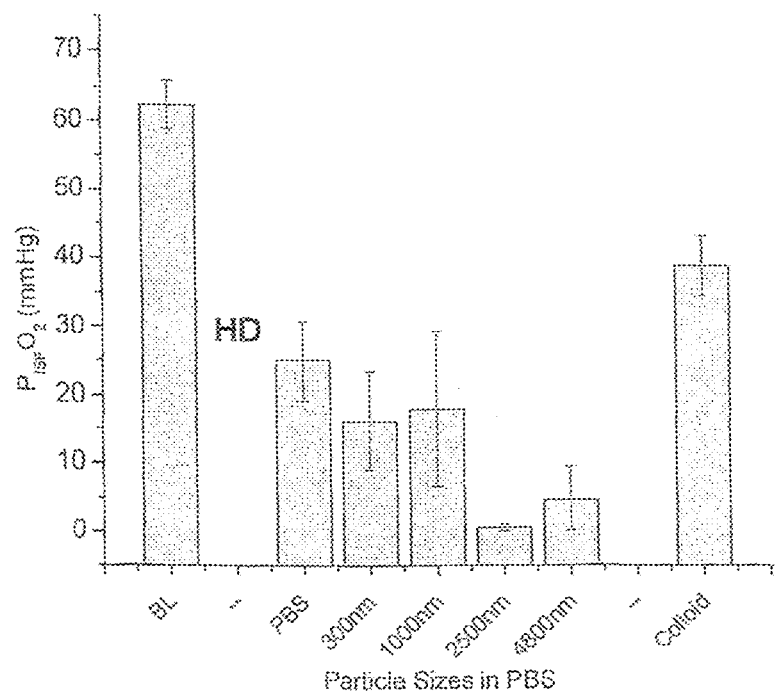

Control 0.25mg/ml

REDUCING THE PROLIFERATION OF ADENOCARCINOMA CELLS (CACO-2) BY ADMINISTRATION OF A POLY-OXYGENATED METAL HYDROXIDE

CLAIM OF PRIORITY

This application is a Continuation-in-Part (CIP) of U.S. patent application U.S. Ser. No. 15/797,972 filed Oct. 30, 2017, entitled REDUCING THE PROLIFERATION OF CARCINOMA CELLS BY ADMINISTRATION OF A POLY-OXYGENATED METAL HYDROXIDE, which is a Continuation-in-Part (CIP) of U.S. patent application U.S. Ser. No. 15/183,403 filed Jun. 15, 2016, entitled INTRAVENOUS ADMINISTRATION OF AN OXYGEN-ENABLE FLUID, which claims priority of U.S. Provisional Patent Application U.S. Ser. No. 62/315,524 entitled OXYGEN-ENABLED RESUSCITATIVE FLUID filed Mar. 30, 2016, the teachings of which are incorporated herein by reference in their entirety.

TECHNICAL FIELD

This disclosure is directed to a method of delivering an oxygen-enabled solution to a mammal to reduce the proliferation of carcinoma.

BACKGROUND

When blood is lost, the chief immediate need is to cease further blood loss followed by replacing the lost blood volume. This critical need is important for allowing the remaining red blood cells to oxygenate body tissue albeit at a reduced capacity. When the body detects the lower hemoglobin levels, from extreme blood loss, compensatory mechanisms begin. There are currently no resuscitative fluids that provide oxygen to hypoxic cells and tissues following major blood loss.

Oxygen therapeutics have traditionally been categorized as either hemoglobin-based oxygen carriers (HBOCs) or perfluorocarbons (PFCs). Unlike blood, HBOCs and PFCs do not require blood typing, have a long shelf life, do not transmit blood borne diseases, and in most cases do not need refrigeration. Despite these promising attributes the widespread utility of HBOCs and PFCs has been limited by concerns regarding hypertension from systemic arteriolar constriction and leukocyte activation, respectively.

Mammals with carcinoma suffer from the proliferation of carcinoma cells. Many such carcinoma cells are hypoxic.

SUMMARY

A method of treating a mammal, comprising administering a therapeutically effective amount of a poly-oxygenated metal hydroxide composition to a mammal to reduce a proliferation of hypoxic carcinoma cells, wherein the poly-oxygenated metal hydroxide composition comprises a clathrate containing free oxygen gas ($O_2$) molecules. The carcinoma cells may comprise colon adenocarcinoma cells (CaCo-2). The poly-oxygenated metal hydroxide material is configured to provide bioavailable oxygen molecules to a mammal when administered to the mammal. The poly-oxygenated metal hydroxide composition can be administered intravenously, directly to carcinoma cells, and orally. The composition may comprise a fluid, where the poly-oxygenated metal hydroxide composition is soluble in the fluid.

BRIEF DESCRIPTION OF THE DRAWINGS

FIG. 3B shows tissue oxygenation ($P_{ISF}$ $O_2$) following 50% volume replacement using Ox66™ in a crystalloid, using particles smaller than those in FIG. 3B, and further shows tissue oxygenation using PEGylated Ox66™ particles in a Colloid;

DESCRIPTION OF EXEMPLARY EMBODIMENTS

Figure 1:
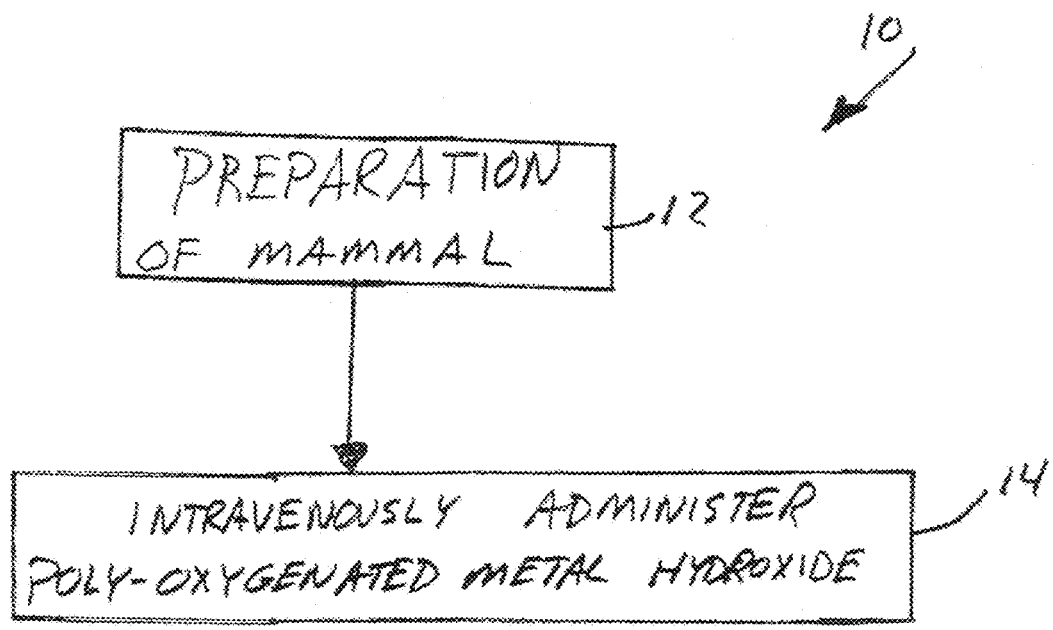
FIG. 1 illustrates a method of intravenously administering a mammal a therapeutically effective amount of a poly-oxygenated metal hydroxide in accordance with this disclosure.
Figure 2A:
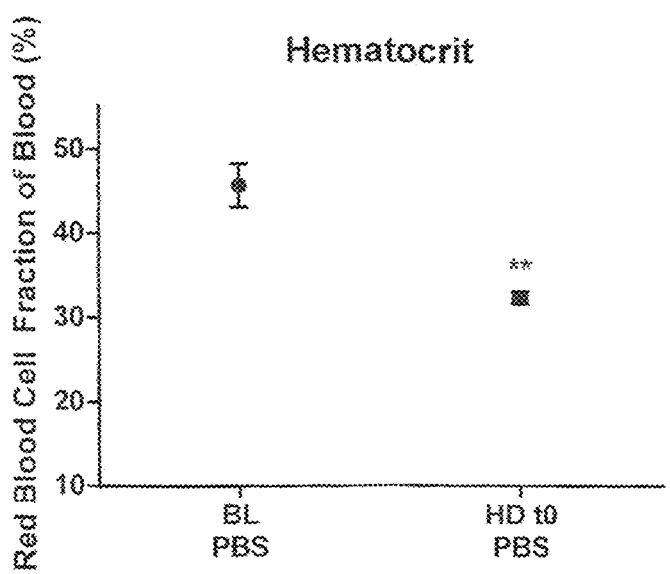
FIGS. 2A-2D are diagrams illustrating systemic characteristics of 50% isovolemic hemodilution, including hematocrit, heart rate, mean arterial pressure, and pulse pressure. Measurements were taken immediately prior to (BL) and following (HD t0) hemodilution.
Figure 2B:
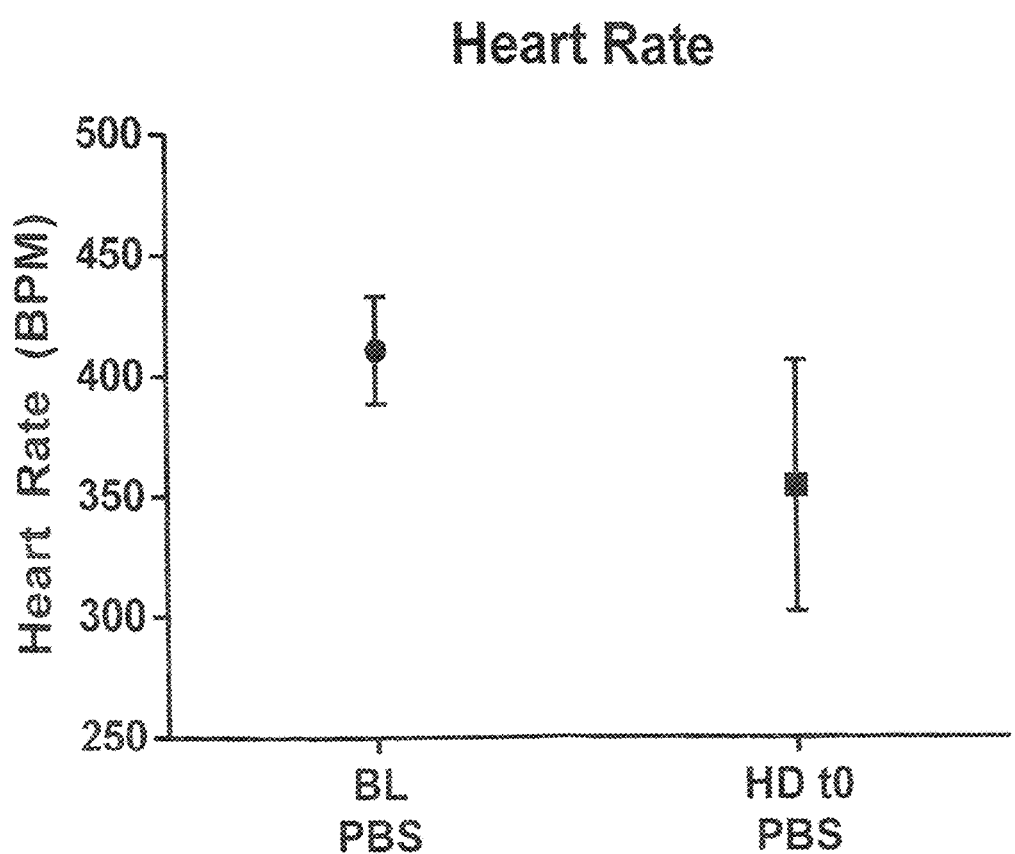
Figure 2C:
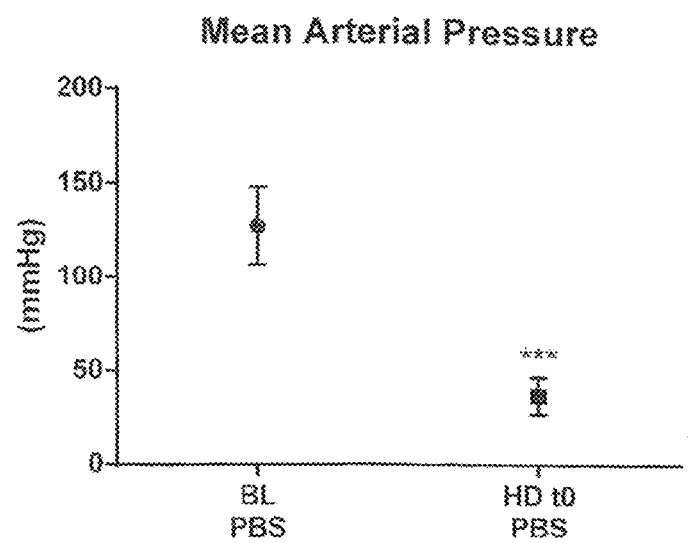
Figure 2D:
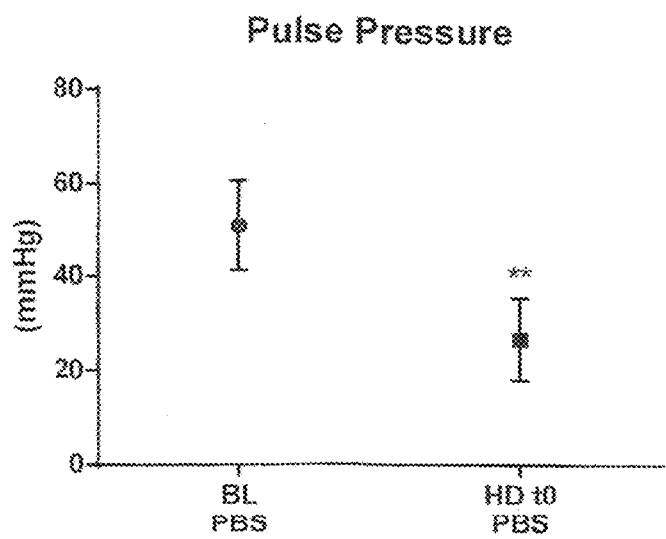

The following description of exemplary embodiments provides information that enables a person skilled in the art to make and use the subject matter set forth in the appended claims, but may omit certain details already well-known in the art. The following detailed description is, therefore, to be taken as illustrative and not limiting.

The example embodiments may also be described herein with reference to spatial relationships between various elements or to the spatial orientation of various elements depicted in the attached drawings. In general, such relationships or orientation assume a frame of reference consistent with or relative to a patient in a position to receive treatment. However, as should be recognized by those skilled in the art, this frame of reference is merely a descriptive expedient rather than a strict prescription.

Despite what is known from physiological principles, there is no practice-based evidence to suggest colloid solutions offer substantive advantages over crystalloid solutions with respect to hemodynamic effects. In addition, there is no evidence to recommend the use of other semisynthetic colloid solutions. Balanced salt solutions are reasonable initial resuscitation fluids, although there is limited practice-based evidence regarding their safety and efficacy. Additionally, the safety of hypertonic solutions has not been established. Ultimately, the selection of the specific resuscitative fluid should be based on indications, contraindications, and potential toxic effects in order to maximize efficacy and minimize toxicity. In addition, the capability of a resuscitative fluid to carry oxygen, as well as to maximize efficacy and minimize toxicity, is desperately needed.

According to this disclosure, there is a significant therapeutic benefit to intravenously oxygenate blood of a human individual and animal, collectively mammals, and create a more effective resuscitative fluid using a poly-oxygenated metal hydroxide, and particularly nano-sized poly-oxygenated aluminum hydroxide, such as Ox66™ oxygen carrying particles manufactured by Hemotek, LLC of Plano, Tex. Ox66™ is an oxygen carrying powder that contains about 66% oxygen, and includes a true clathrate that is a lattice-like structure that provides large areas capable of capturing and holding $O_{2(g)}$ oxygen gas. The Ox66™ poly-oxygenated aluminum hydroxide has a molecular formula $Al_{12}H_{42}O_{36}$, and the $O_{2(g)}$ oxygen gas molecules are bioavailable to, and used by the body, because the $O_{2(g)}$ oxygen gas molecules are not bound in the hydroxide complex. Ox66™ exists under STP (standard temperature and pressure) as a poly-oxygenated aluminum hydroxide comprising a clathrate, and chlorine. The molecular formula $Al_{12}H_{42}O_{36}$ is mathematically reduced to the molecular formula $Al(OH)_3 \cdot 6O_2$. The 6 free oxygen gas molecules ($O_{2(g)}$) are separate from the oxygen molecules covalently bound in the hydroxide complex. The hydrogen is effervescent. The poly-oxygenated aluminum hydroxide is soluble in a fluid.

This disclosure significantly increases tissue oxygenation of the mammal, known as oxygen tension $PO_2$. In certain applications of Ox66™, the $PO_2$ levels of a hemo-diluted mammal can exceed baseline. Fluid resuscitation with colloid and crystalloid solutions is a global intervention in acute medicine, and while the selection and ultimate use of resuscitation fluids is based on physiological principles, clinician preference determines clinical use. Studies have shown that Ox66™ does not create any negative effects in toxicology studies where Ox66™ was either injected or gavaged in a mammal.

With enough blood loss, like in amputations and other military trauma situations, red blood cell levels drop too low for adequate $PO_2$ tissue oxygenation, even if volume expanders maintain circulatory volume they do not deliver oxygen. In these situations, the only currently available alternatives are blood transfusions, packed red blood cells, or a novel oxygen-enabled resuscitative fluid according to this disclosure.

This disclosure provides a novel oxygen-enabled blood additive, also referred to as a resuscitative fluid, that can effectively oxygenate mammal tissues and provide essential elements to protect and save critical cells and tissues, and the mammal itself. This disclosure is desperately needed on the battlefield, as well as in civilian trauma cases. One exemplary formulation consists of a fluid of 75-90% colloid or crystalline solutions with 10-25% addition of a poly-oxygenated metal hydroxide material, such as but not limited to, nano-sized Ox66™ particles, resulting in concentration ranges of 0.1 mg/l to 1000 mg/l. For use as a blood additive, ideal sizes of the Ox66™ particles may be between 10 nm to 100 μm in size, depending on the treatment. To avoid immune response, it is critical in some treatments that the diameter of the Ox66™ particles should ideally be less than 300 nm as these particle sizes have less potential for toxicity and maximized efficacy The blood additive compositions can include surface modifications of nano-sized poly-oxygenated metal hydroxide particles with polyethylene glycol (PEG) for increased vascular transit, protein for increased surface to volume ration, or specific charge to enhance absorption and sustained $PO_2$. These modifications of the poly-oxygenated metal hydroxide material as a blood additive extend the oxygenating capabilities of the material for longer periods of time, thus extending product life, such as specifically in far-forward combat theatres.

This blood additive composition is extremely significant because the blood additive is agnostic to the blood type of a mammal, meaning that the blood additive can be administered to a human individual without typing the human individual's blood. Thus, even individuals with rare blood types can be effectively treated with the same blood additive. There is no time delay as the blood additive can be immediately administered to an individual in a crisis situation. Further, the blood additive has significant shelf life and can be stored at room temperature in locations where administration of the blood additive can be performed in emergency situations, such as in the battlefield to extend a soldier's life until the soldier can be transported to a quality hospital, or in an ambulance or fire truck. Stabilizing a human individual for hours or even minutes can save a human individual's life.

As shown in FIG. 1, this exemplary embodiment comprises a method 10 of intravenously administering a mammal a therapeutic amount of a composition including a poly-oxygenated metal hydroxide, such as a human individual, or an animal. The poly-oxygenated metal hydroxide composition may comprise a poly-oxygenated aluminum hydroxide, such as Ox66™ particles. One method includes administration of a therapeutically effective resuscitative fluid to increase tissue oxygenation $PO_2$ in the mammal. Another method can include administration of a therapeutically effective composition to treat a condition of a mammal. The method comprises preparing a mammal at step 12, such as preparing a site on the mammal for receiving a catheter, and intravenously administering a poly-oxygenated metal hydroxide composition at step 14, such as using a catheter. Various methods and treatments are detailed as follows.

Study

A preclinical study was performed to ascertain the efficacy of a poly-oxygenated metal hydroxide in a mammal, comprising Ox66™ particles, and the details of the study and results are included. For this study, Particle Size A diameter is 100 um and Particle Size B diameter is 10 um.

In this study, male Sprague-Dawley rats underwent a 50% blood volume isovolemic hemodilution exchange with either Ox66™ or phosphate buffered saline (PBS; volume control), since Ox66M was suspended in PBS, such as lactated Ringers solution (LRS). LRS is a crystalloid electrolyte sterile solution of specified amounts of calcium chloride, potassium chloride, sodium chloride, and sodium lactate in water for injection. LRS is typically is used intravenously to replace electrolytes. Isovolemic hemodilution is the reduction of red blood cells (hematocrit) with an equal volume of hemodiluent, i.e., crystalloids, colloids or oxygen therapeutics.

The withdrawal/infusion rate was 2.0 ml×min$^{-1}$×kg$^{-1}$ and performed through a cannulated carotid artery and jugular vein. Systemic measurements were recorded via a cannulated femoral artery that was connected to a pressure transducer (MP150; Biopac Systems, Inc, Goleta, Calif.), while microcirculatory parameters were collected through phosphorescence quenching and intravital microscopic examination of the exteriorized spinotrapezius muscle. Compared to baseline, a 50% blood volume exchange with either hemodiluent caused a reduction in heart rate, blood pressure, arterial diameter and interstitial fluid (ISF) oxygen tension ($PO_2$) in all animals. However, Ox66™ animals demonstrated an improvement in ISF $PO_2$ compared to PBS animals. This finding demonstrates that Ox66™ both transports and releases oxygen to the peripheral microcirculation.

Animals
   Male Sprague Dawley rats (250-300 g)
Anesthetics
   Isoflurane (induction)
   Alfaxalone (continuous rate of infusion)
Surgical Preparation
   Vessels and tracheal cannulation
   Spinotrapezius muscle exteriorized
Systemic Parameters
   BIOPAC MP150 (real-time analysis)
Tissue Oxygenation
   Phosphorescence Quenching Microscopy
      Palladium porphyrin (RO) probe distributed into interstitium.
      Phosphorescence decay curve captured and fit to standard curve for translation to $P_{ISF}\,O_2$ in mmHg.
Hemodilution (HD)
   Baseline parameters collected
   50% isovolemic exchange of blood with test solution at 2.0 ml/kg/min
   Post-HD parameters collected
   Animals observed for 2 h post-HD
Hemodiluents
   Phosphate Buffered Saline (PBS)
   Ox66™ Size A [1×]
   Ox66™ Size A [10×]
   Ox66™ Size B [1×]
   Ox66™ Size B [10×]

FIGS. 2A-2D show systemic characteristics of 50% isovolemic hemodilution (HID). Measurements were taken immediately prior to baseline (BL) and following hemodilution at (HD t0). The volume exchange of whole blood with PBS (vehicle volume control) resulted in significant reductions in hematocrit, mean arterial pressure, and pulse pressure. The reduction in heart rate lacked statistical strength.  $p<0.01$, * $p<0.001$.

Figure 3A:
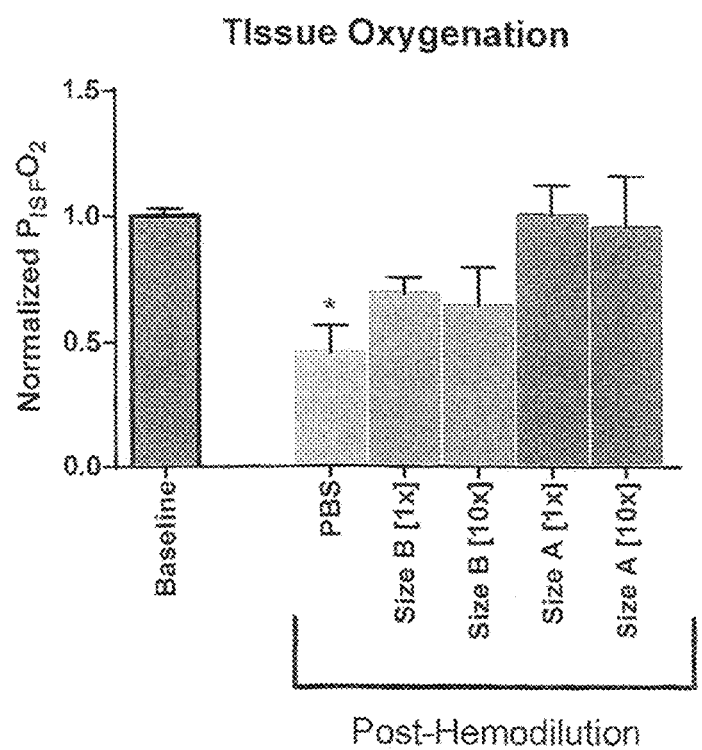
FIG. 3A shows tissue oxygenation ($P_{ISF}$ $O_2$) following 50% volume replacement using Ox66™ in a crystalloid. All $P_{ISF}$ $O_2$ values (mmHg) were normalized to baseline (BL) for ease of comparison.

FIG. 3A shows tissue oxygenation ($P_{ISF}\,O_2$) following 50% volume replacement. All $P_{ISF}\,O_2$ values (mmHg) were normalized to baseline (BL) for ease of comparison. PBS alone was used as a vehicle volume control. Ox66™ compounds were suspended in PBS as crystalloids, where particle size A was 10× larger than particle size B and trended towards higher oxygen delivery. Both particle sizes were assessed at 1× and 10× concentrations, but failed to show a concentration dependence of $P_{ISF}\,O_2$ in this range. * $p<0.05$ vs BL. Particle Size A diameter is 100 um and Particle Size B diameter is 10 um.

FIG. 3B shows tissue oxygenation ($P_{ISF}\,O_2$) following 50% volume replacement. All $P_{ISF}\,O_2$ values (mmHg) were normalized to baseline (BL) for ease of comparison. PBS alone was used as a vehicle volume control. FIG. 3B shows Ox66™ particles diameters being smaller than those shown in FIG. 3A that were suspended in PBS as crystalloids, having sizes of 300 nm, 1000 nm (1 um), 2500 nm (2.5 um), and 4800 nm (4.8 um), compared to the PBS alone. Compared to the results shown in FIG. 3A, Ox66™ particles having a diameter of around 10 urn suspended in PBS as a crystalloid appear to achieve a superior increase in $P_{ISF}\,O_2$ values (mmHg).

Figure 3C:
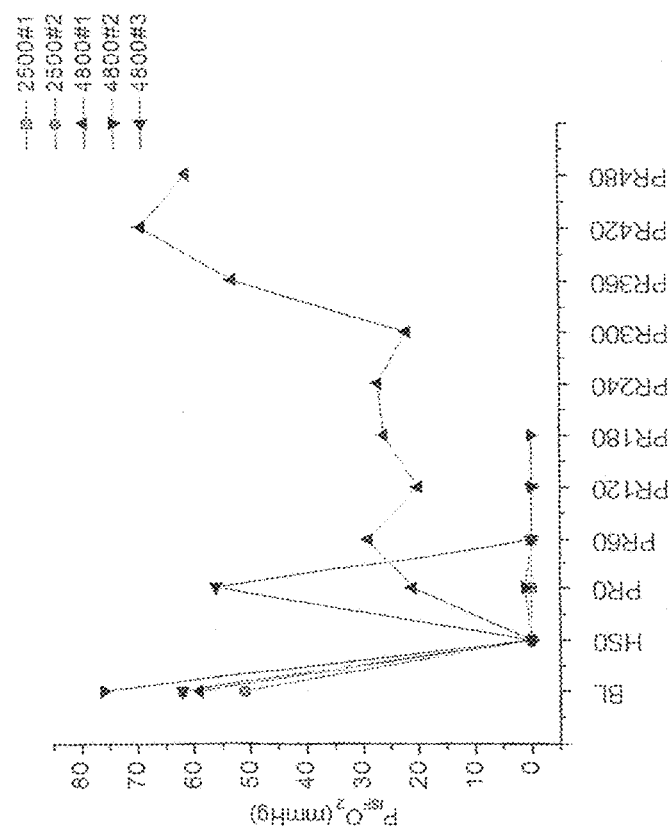
FIG. 3C shows survival results of specimens after undergoing hemorrhagic shock following resuscitation using PEGylated Ox66™ particles in a Colloid, including complete survival of one specimen.

FIG. 3B also shows Ox66™ particles suspended in a Colloid that results in vastly improved $P_{ISF}\,O_2$ values (mmHg) compared to PBS alone, and also compared PBS including Ox66™ particles as a crystalloid having reduced size particles, as shown. This is due in part to the blood additive composition including surface modifications of the nano-sized poly-oxygenated metal hydroxide particles with polyethylene glycol (PEG) for increased vascular transit, protein for increased surface to volume ration, and/or specific charge to enhance absorption and sustained $PO_2$. The PEGylation particles have a spherical shape that makes them more slippery which results in better capillary transit and less irritation of the capillaries. The PEGylation also serves as an aggregate inhibitor. These modifications of the poly-oxygenated metal hydroxide material as a blood additive provides increased concentration control and extends the oxygenating capabilities of the material for longer periods of time, thus extending product life, such as specifically in far-forward combat theatres, FIG. 3C shows the results of resuscitation of five male Sprague-Dawley rat specimens after hemorrhagic shock. As shown, two specimens underwent resuscitation with a Colloid including 2.4 um Ox66™ PEGylation particles, and each specimen survived 1 hour after hemorrhagic shock. This is significant as death would have occurred within 10 minutes of hemorrhagic shock.

Even more significant, one of the three specimens that underwent resuscitation with a Colloid including 4.8 um Ox66™ PEGylation particles showed a significant immediate increase in $P_{ISF}\,O_2$, and survived 8 hours after hemorrhagic shock, when the monitoring was completed and the specimen continued to survive, a complete survival. A second specimen showed a significant immediate increase in $P_{ISF}\,O_2$ and survived 3 hours. The third specimen also survived an additional 3 hours. This significant survival of all five specimens after hemorrhagic shock by resuscitating each with a Colloid including Ox66™ PEGylation particles is remarkable. Advantageously, survival from hemorrhagic shock without using a blood product is extremely encouraging, as the Colloid does not require blood typing. When used on individuals on the battlefield, this survival time is significant and allows transport of an individual that undergoes hemorrhagic shock to a treatment facility.

Figure 4A:
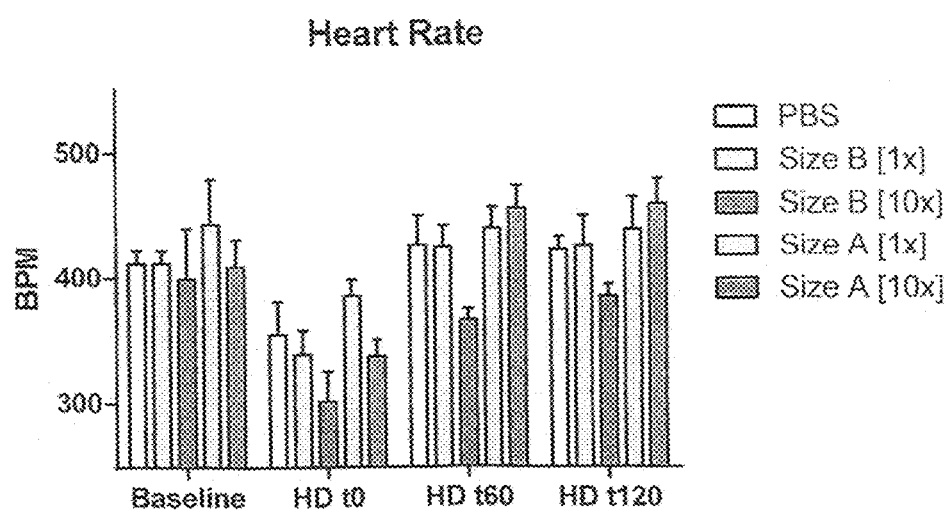
FIGS. 4A and 4B show systemic parameters including heart rate and mean arterial pressure following isovolemic hemodilution with test solutions.
Figure 4B:
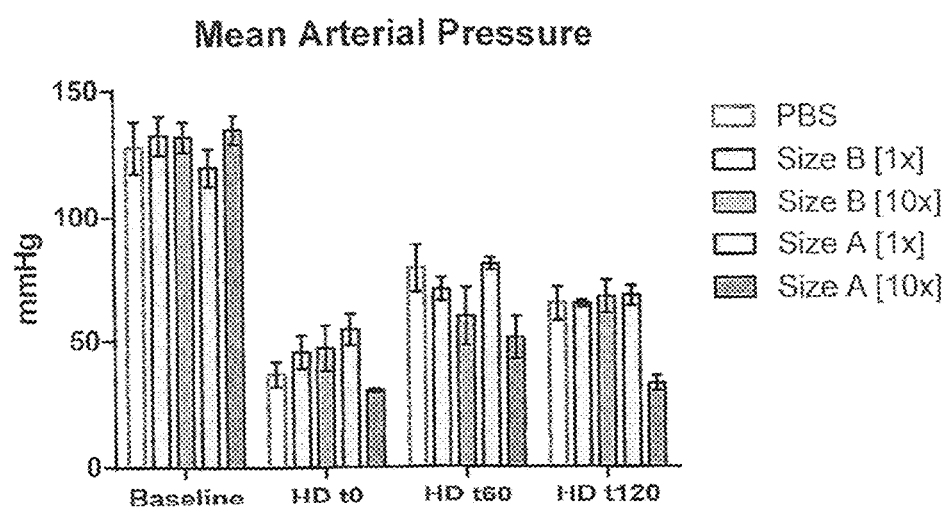

FIGS. 4A and 4B shows systemic parameters following isovolemic hemodilution with test solutions. HD=Hemodilution; tn=time point in minutes following hemodilution. As shown in FIG. 4A, heart rates generally followed the scheme of slowing down by HD t0 and then returning to baseline by t60. As shown in FIG. 4B, mean arterial pressure remained low, but stable following hemodilution with the exception of Size A at 10× concentration. Statistical tests were not performed due to low sample sizes (N=2-4).

Figure 5:
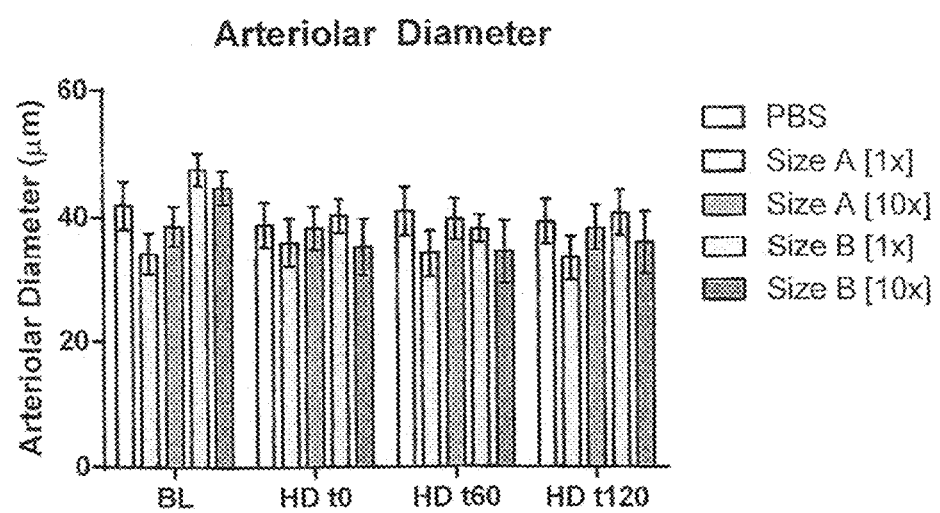
FIG. 5 shows arteriolar luminal diameters. Arterioles included were smaller than 60 microns at baseline.

FIG. 5 shows arteriolar luminal diameters. Arterioles included were smaller than 60 microns at baseline.

SUMMARY

The '50% Isovolemic Hemodilution' model produces a good reduction in systemic cardiovascular parameters and tissue oxygenation to assess therapeutic potential of interventions.

Ox66™ is capable of carrying and delivering oxygen to hypoxic peripheral tissues.

Administering Surface Modified Ox66™ Particles

In an exemplary embodiment, the administered Ox66™ particles may be surface modified for specific therapeutic uses such as time release, PEGylation, growth factor modification, antibacterial, antimicrobial, protein modification, and enzymes.

Treatment of Traumatic Brain Injury (TBI), Strokes, and CTE

To achieve microcirculation in mammals, such as to treat TBI and strokes, the Ox66™ particles preferably have a diameter of less than 300 nm to pass the blood brain barrier (BBB). The upper limit of pore size enabling passive flow across the BBB is usually <300 nm; however, particles having a diameter of several nanometers can also cross the BBB via carrier-mediated transport using specialized transport proteins. Alternatively, receptor-mediated transport can act as an "escort" for larger particles. This exemplary embodiment comprising intravenously administering a therapeutic amount of a composition including Ox66™ particles having a diameter of less than 300 nm is therapeutically effective in treating a mammal with TBI and BBB. This is an extraordinary accomplishment, and can revolutionize the treatment of not only TBI and BBB, but also other brain conditions/injury including Chronic Traumatic Encephalopathy (CTE), which is a progressive degenerative disease of the brain found in athletes, military veterans, and others with a history of repetitive brain trauma.

Treatment of Diabetes

To achieve microcirculation in mammals to treat Diabetes, this exemplary embodiment comprises intravenously administering to a mammal a therapeutic amount of a composition including Ox66™ particles as a fluid that is therapeutically effective to increase $PO_2$ in the mammal, such as a human individual, or an animal, to reduce the effects of Diabetes.

Treatment of Carcinoma

To treat cancer in mammals, exemplary embodiments comprise intravenously administering to a mammal a therapeutic amount of a composition including Ox66™ particles as a fluid that is therapeutically effective to reduce the effects of, or eliminate, cancer cells in the mammal, such as a human individual, or an animal. The composition Ox66™ can also be administered orally to the mammal.

The charts in the Figures described hereafter illustrate laboratory results of the proliferation of the identified carcinoma after administration of various concentrations of the Ox66™ in a fluid to living carcinoma cells compared to control, which is no administration of the Ox66™ to the cells.

For the following results, three assays are used: Janus Green (JG) colorimetric assay, Lactase Dehydrogenase (LDH) colorimetric assay, and CFDA-5 fluorometric assay.

Janus Green (JG) is a supravital stain, meaning it is absorbed by damaged cells. It is not able to penetrate healthy cells, but when cells are damaged or dead, it is able to pass easily into the cell, and stain the mitochondria. Janus Green is a relatively quick way to assess the heath of cells, and it must be used in two parts; one plate for viability, and the other for proliferation in order to obtain a percent viability of cells. The measurements are not exact numbers, but rather an estimate based on professional observation.

Janus Green Protocol:

Obtain two (2) 96-well plates (one plate for viability, the other plate for proliferation). Seed ~1 Million identified living carcinoma cells per plate.

Once the carcinoma cells have reached 50% confluency (~24 hours), dose the cells in the plates with varying concentrations of Ox66™ fluid (2 columns of cells for each concentration of Ox66™ including control).

After 24 hours, run JG.

Standard Protocol was followed:

For the viability, the cells were stained with JG dye before being fixed with 100% ethanol. This shows which cells were still alive.

For the proliferation, the cells were fixed with 100% ethanol before being stained with JG to get an approximate number of how many cells were seeded.

The plates were then run in a colorimetric plate reader.

Lactate dehydrogenase is an enzyme that is present in all living cells, and is released when cell membrane integrity is compromised, making this assay, which detects the presence of LDH a reliable option for cytotoxicity. The LDH assay uses the compound iodonitrotetrazolium (INT) to react with LDH present to form a red colored formazan. This react can then be read under a colorimetric plate reader and be quantified.

LDH Protocol:

Seed and dose the carcinoma cells the same as for JG, with only one 96-well plate.

50 microliters of cell media are taken from each well and placed into a new well plate, then 50 microliters of LDH solution is added to the new well plate, along with the media.

The plate was then run in a colorimetric plate reader.

5-CFDA, AM assay is an enzymatic marker assay, as well as a cell membrane permeability marker. Enzymatic activity present within the cells will cause the CFDA dye to fluoresce, and the cell membrane integrity will retain the fluoresced product within the cell.

5-CFDA, AM Protocol:

Seed and dose the cells the same as for LDH.

The cells are stained with the CFDA dye and are incubated for ~30 minutes, then the solution is diluted with media, and read under a fluorescent plate reader.

Study 1—Liver Carcinoma (HEPG-2)

Figure 6:
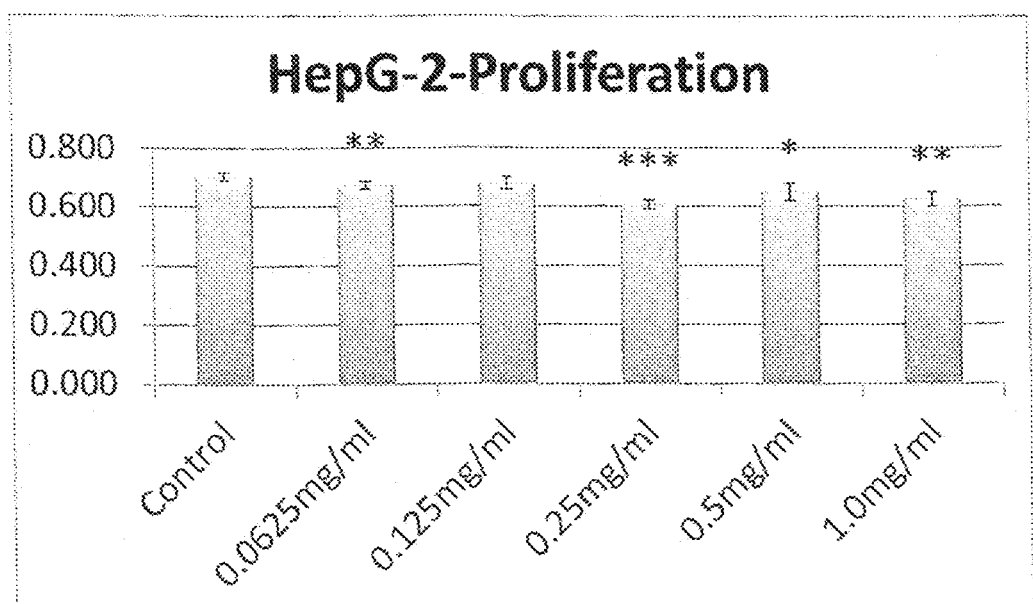
FIG. 6 shows the proliferation of hepatocarcinoma cells (HEPG-2) significantly reduced following administration with various concentrations of Ox66™.

The proliferation of hepatocarcinoma cells (HEPG-2) was significantly reduced following administration of various concentrations of Ox66™ to the cells, as shown in FIG. 6. A hypoxic microenvironment, which is a common feature of hepatocellular carcinoma can induce HIF-1α expression and promote the epithelial-mesenchymal transition (EMT). Additionally, it can induce the invasion of cancer cells. This proven characteristic of hepatocarcinoma supports the hypothesis that Ox66™ is effective in reducing the proliferation of these cells.

Figure 7A:
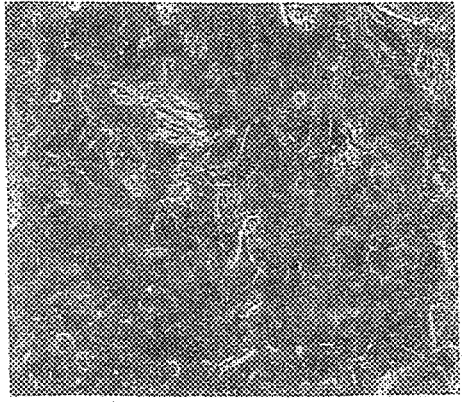
FIG. 7A and FIG. 7B illustrate images of cells HEPG-2 cells prior to dosing and after dosing, respectively.
Figure 7B:
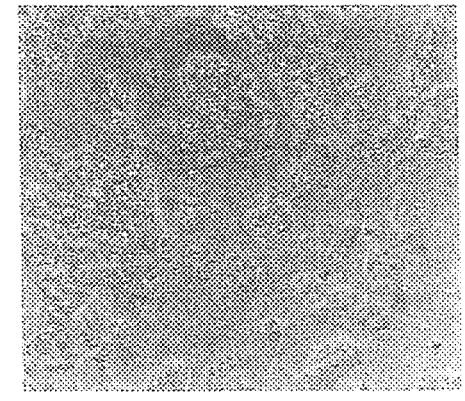

Images shown in FIG. 7A and FIG. 7B illustrate HEPG-2 cells prior to dosing and after dosing with Ox66™ fluid, respectively.

Study 2—Prostate Carcinoma (22Rv1)

Figure 8:
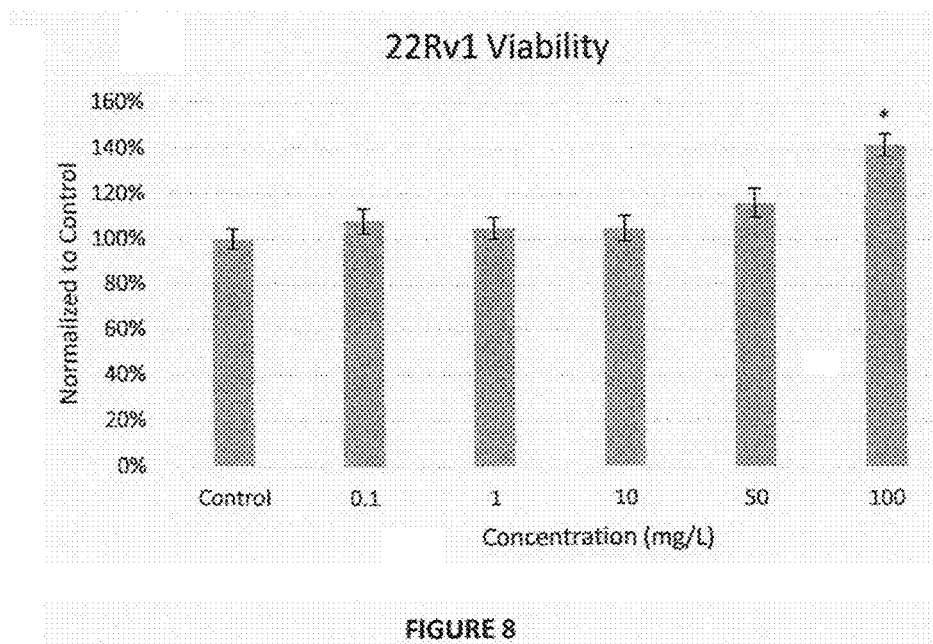
FIG. 8 shows the proliferation of prostate carcinoma cells (22Rv1) significantly reduced following administration with various concentrations of Ox66™.

The proliferation of prostate carcinoma (22Rv1) cells was significantly reduced following administration with various concentrations of Ox66™ fluid to the cells, as shown in FIG. 8. Prostate carcinoma cells are hypoxic, which helps explain why Ox66™ is effective in reducing the proliferation of these cells.

For this cell line, 22Rv1 (prostate carcinoma), the Janus Green colorimetric assay was used to determine how viable the cells were after being dosed with varying concentrations of the Ox66 ™ into the cell culture media. This administration is similar to injection into the blood stream as would be given via an intravenous injection (IV). Janus Green is an exclusion dye, which only stains mitochondria and nuclei of damaged cells. For the assay, the cell culture was washed twice with phosphate buffered saline (PBS), followed by one minute fixation with absolute ethanol. The culture was then subjected to one-minute staining by Janus Green B dye solution followed by two PBS wash to remove the excess dye. Then the encapsulated dye from these cells was extracted with absolute ethanol, and an additional 100 ul water was added to each well to maintain samples. Optical intensity was then read at 630 nm on a microplate reader. Janus Green gives intensive staining of the nuclei with light staining of the cytoplasm, thus outlining cells clearly. Therefore, morphologic changes of cells can also be screened after the assay using an inverted microscope. The more Janus Green present, the more damaged or dead cells are present as well. The graph shows that for administration of Ox66™ fluid to the cells at a concentration of 100 mg/L, there is a statistical difference between the uptake of Janus Green at 100 mg/L than at 0 mg/L, or the control. This is the only concentration that is statistically different when compared to the control for this carcinoma.

Study 3—Lung Carcinoma (A549)

Figure 9:
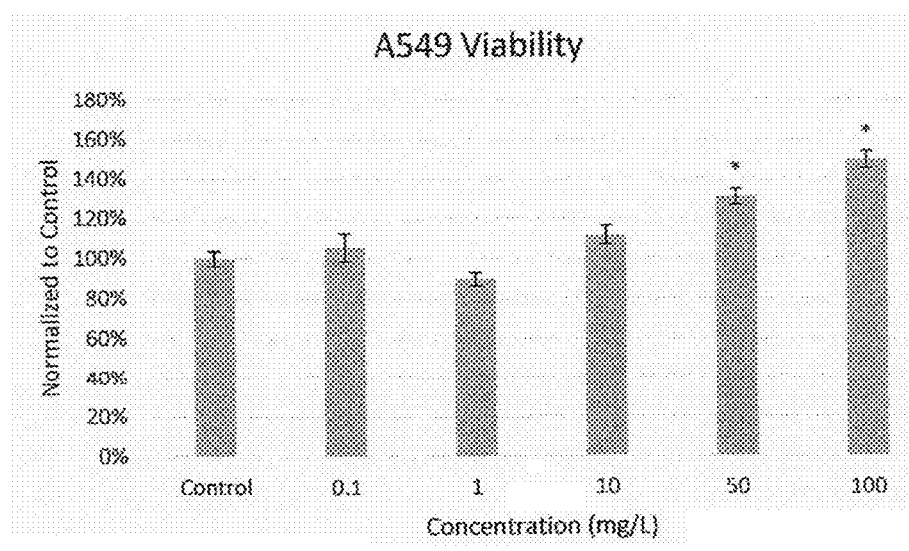
FIG. 9 shows the proliferation of lung carcinoma cells (A549) significantly reduced following administration with various concentrations of Ox66™.

The proliferation of lung carcinoma (A549) cells was significantly reduced following administration with various concentrations of Ox66™ fluid to the cells, as shown in FIG. 9. Lung carcinoma cells are hypoxic, which helps explain why Ox66™ is effective in reducing the proliferation of these cells.

For this cell line, A549 (lung carcinoma), the Janus Green colorimetric assay was used to determine how viable the cells were after being dosed with varying concentrations of Ox66™ into the cell culture media. This administration is similar to injection into the blood stream as would be given via an intravenous injection (IV). Janus Green is an exclusion dye, which only stains mitochondria and nuclei of damaged cells. For the assay, the cell culture was washed twice with phosphate buffered saline (PBS), followed by one minute fixation with absolute ethanol. The culture was then subjected to one-minute staining by Janus Green B dye solution followed by two PBS wash to remove the excess dye. Then the encapsulated dye from these cells was extracted with absolute ethanol, and an additional 100 ul water was added to each well to maintain samples. Optical intensity was then read at 630 nm on a microplate reader. Janus Green gives intensive staining of the nuclei with light staining of the cytoplasm, thus outlining cells clearly. Therefore, morphologic changes of cells can also be screened after the assay using an inverted microscope. The more Janus Green present, the more damaged or dead cells are present as well. The graph shows that for the administration of Ox66™ at 50 mg/L and 100 mg/L there is a statistical difference between the uptake of Janus Green at 50 mg/L and 100 mg/L than at 0 mg/L, or the control. This indicates that these carcinoma cells are more receptive to the Ox66™ treatment than 22Rv1 cells.

Study 4—Colon Adenocarcinoma (CaCo-2)

Figure 10:
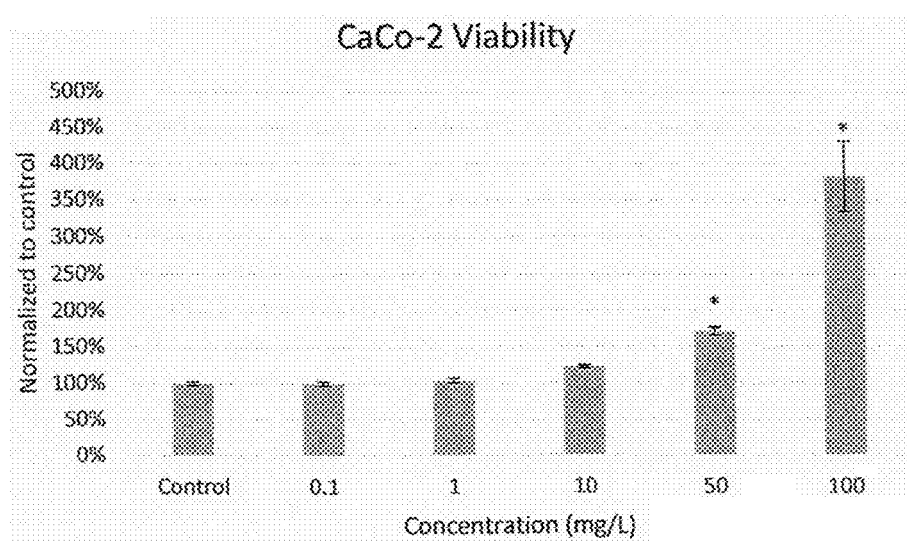
FIG. 10 shows the proliferation of colon adenocarcinoma cells (CaCo-2) significantly reduced following administration with various concentrations of Ox66™.

The proliferation of colon adenocarcinoma cells (CaCo-2) was significantly reduced following administration with various concentrations of Ox66™ in the culture media of the cells, as shown in FIG. 10. Colon adenocarcinoma cells are hypoxic, which helps explain why Ox66™ is effective in reducing the proliferation of these cells.

For this cell line, CaCo-2 (colon adenocarcinoma), the Janus Green colorimetric assay was used to determine how viable the cells were after being dosed with varying concentrations of Ox66™ into the cell culture media. This administration is similar to injection into the blood stream as would be given via an intravenous injection (IV). fluid. Janus Green is an exclusion dye, which only stains mitochondria and nuclei of damaged cells. For the assay, the cell culture was washed twice with phosphate buffered saline (PBS), followed by one minute fixation with absolute ethanol. The culture was then subjected to one-minute staining by Janus Green B dye solution followed by two PBS wash to remove the excess dye. Then the encapsulated dye from these cells was extracted with absolute ethanol, and an additional 100 ul water was added to each well to maintain samples. Optical intensity was then read at 630 nm on a microplate reader. Janus Green gives intensive staining of the nuclei with light staining of the cytoplasm, thus outlining cells clearly. Therefore, morphologic changes of cells can also be screened after the assay using an inverted microscope. The more Janus Green present, the more damaged or dead cells are present as well. The graph shows that for administration of Ox66™ at 50 mg/L and 100 mg/L there is a statistical difference between the uptake of Janus Green at 50 mg/L and 100 mg/L than at 0 mg/L, or the control. This indicates that these cells are more receptive to Ox66™ than 22Rv1 cells. There is a substantial jump in uptake of the Janus Green at 100 mg/L, meaning there were many more damaged cells at this concentration.

Erectile Dysfunction

To achieve the treatment of erectile dysfunction in mammals, this exemplary embodiment comprises intravenously administering to a mammal a therapeutic amount of a composition including Ox66™ particles that is therapeutically effective to increase oxygenated blood flow thus mitigating physical dysfunction in the mammal, such as a human individual, or an animal, to reduce the effects of erectile dysfunction. In another embodiment, the Ox66™ particles could be embodied in a tablet or capsule form and administered orally.

Sickle Cell Anemia

To achieve the treatment of sickle cell anemia in mammals, this exemplary embodiment comprises intravenously administering to a mammal a therapeutic amount of a composition including Ox66™ particles (~0.07 μm) that is therapeutically effective to increase oxygenated blood flow thus mitigating dysfunction in the mammal, such as a human individual, or an animal, to reduce the effects of sickle cell anemia. In another embodiment, the Ox66™ particles could be embodied in a tablet or capsule form and administered orally. In sickle cell anemia, the red blood cells become rigid and tacky and are shaped like sickles hence the name of the disease. These irregularly shaped "sickle" cells do not move through small blood vessels, resulting in slowing or blockage of blood flow and oxygen to parts of the body. This embodiment of Ox66M particles could oxygenate the body in a crisis and act as an alleviation strategy for sickle cell anemia.

Bronchopulmonary Dysplasia (BPD)

To treat bronchopulmonary dysplasia in mammals, this exemplary embodiment comprises intravenously administering to a mammal a therapeutic amount of a composition including Ox66™ particles as a fluid that is therapeutically effective to reduce the effects of, or eliminate, BPD in the mammal, such as a human individual, or an animal. A critical problem facing preterm infants is adequate lung function. Premature babies can have strokes, chronic lung disease and potential brain damage due to small, fragile blood vessels, and pressurized oxygen required after birth to keep the lungs functional. There is a need for an alternative oxygen therapy that mitigates the aforementioned risks. These preemies frequently encounter complications such as chronic lung disease—sometimes called bronchopulmonary dysplasia (BPD). BPD can occur because the infants still have some inflammation in their lungs and may require extra oxygen or medications to help them breathe comfortably.

There are several hyper-oxygenated associated illnesses that a preterm infant will suffer such as retinopathy of prematurity (ROP), periventricular leukomalacia, cerebral palsy, and the previously mentioned bronchopulmonary dysplasia (BPD), to name a few. Administration of Ox66™ provides alternative oxygen delivered by less invasive means yet supplying oxygen to the preterm infant.

Alzheimer's Disease (AD)

To treat Alzheimer's disease in mammals, this exemplary embodiment comprises intravenously administering to a mammal a therapeutic amount of a composition including Ox66™ particles as a fluid that is therapeutically effective to reduce the effects of, or eliminate, AD in the mammal, such as a human individual, or an animal. Alzheimer's disease (AD) is classified as a neurodegenerative disorder. The cause and progression of the disease are not well understood. AD is associated with hallmarks of plaques and tangles in the brain. Current treatments only help with the symptoms of the disease and there are no available treatments that stop or reverse the progression of the disease. As of 2012, more than 1,000 clinical trials have been or are being conducted to test various compounds in AD. There is currently no approved drug therapy for AD that will stop or reverse the progression of the disease. There is a clear link between low oxygen levels in the brain and Alzheimer's disease, but the exact mechanisms behind this are not yet fully understood (Alzheimer's Society, Proceedings of the National Academy of Sciences). A healthy brain needs a good supply of oxygen. A disruption of the blood flow through or to the brain causes low oxygen levels. When there is damage or a blockage, or the blood supply itself is low in oxygen then insufficient oxygen will be delivered to the brain cells. Ox66™ offers the potential of micrometer sized (~0.07 μm) particles increasing oxygen delivery to the brain. With this offloading of oxygen, there is significant potential to mitigate the development and/or the progression of AD.

Autism

To treat autism in mammals, this exemplary embodiment comprises intravenously administering to a mammal a therapeutic amount of a composition including Ox66™ particles as a fluid that is therapeutically effective to reduce the effects of, or eliminate, autism in the mammal,

What is claimed is:

1. A method of treating a mammal, comprising administering a therapeutically effective amount of a poly-oxygenated aluminum hydroxide composition to the mammal in need thereof to reduce a proliferation of colon adenocarcinoma CaCo-2 cells, wherein the poly-oxygenated aluminum hydroxide composition comprises a clathrate containing fee oxygen gas (O2) molecules; and wherein the therapeutically effective amount of the poly-oxygenated aluminum hydroxide composition ranges from 10 mg/L to 1000 mg/L.

2. The method as specified in claim 1 wherein the poly-oxygenated aluminum hydroxide material is configured to provide bioavailable oxygen gas molecule to the mammal when administered to the mammal.

3. The method as specified in claim 1 wherein the poly-oxygenated aluminum hydroxide composition is administered intravenously.

4. The method as specified in claim 1 wherein the poly-oxygenated aluminum hydroxide composition is administered direct to the colon adenocarcinoma CaCo-2 cells.

5. The method as specified in claim 1 where the poly-oxygenated aluminum hydroxide composition is administered orally.

6. The method as specified in claim 1 wherein the compsition comprises a fluid.

7. The method as specified in claim 1 wherein the poly-oxygenated aluminum hydroxide composition soluble in the fluid.

8. The method as specified claim 6 wherein the fluid is a phosphate buffered saline (PBS).

9. The method as specified in claim 6 wherein the fluid is lactated ringers solution (LRS).

10. The method as specified in claim 1 wherein the poly-oxygenated aluminum hydroxide composition comprises poly-oxygenated aluminum hydroxide particles all having a diameter of less than or equal to 10 um.

11. The method as specified in claim 10 wherein the polyoxygenated aluminum particles are homogeneous.

12. The method as specified in claim 1 wherein the poly-oxygenated aluminum hydroxide composition comprises poly-oxygenated aluminum hydroxide particles all having a diameter of less than or equal to 1 um.

13. The method as specified in claim 1 wherein the poly-oxygenated aluminum hydroxide composition comprises poly-oxygenated aluminum hydroxide particles that are surface modified.

14. The method as specified claim 13 wherein the poly-oxygenated aluminum hydroxide material comprises particles that are surface modified with polyethylene glycol (PEG).

15. The method as specified in claim 1 wherein the mammal is a human individual.

* * * * *